US 6,679,094 B2

(12) United States Patent
Wang et al.

(10) Patent No.: US 6,679,094 B2
(45) Date of Patent: Jan. 20, 2004

(54) CALIBRATION ADAPTER FOR GAS DETECTION INSTRUMENT

(75) Inventors: Annie Q. Wang, Shanghai (CN); Jiangang Chen, Shanghai (CN)

(73) Assignee: Industrial Scientific Corporation, Oakdale, PA (US)

( * ) Notice: Subject to any disclaimer, the term of this patent is extended or adjusted under 35 U.S.C. 154(b) by 191 days.

(21) Appl. No.: 10/068,006

(22) Filed: Feb. 8, 2002

(65) Prior Publication Data

US 2003/0150252 A1 Aug. 14, 2003

(51) Int. Cl.[7] .............................................. G01N 37/00
(52) U.S. Cl. ........................................................ 73/1.06
(58) Field of Search ................................ 73/1.03–1.07

(56) References Cited

U.S. PATENT DOCUMENTS 4,742,708 A * 5/1988 Porter ........................ 73/1.04
5,060,503 A * 10/1991 Spohn et al. ............... 73/1.05

FOREIGN PATENT DOCUMENTS

DE              002645736    * 11/1977    ................. 73/1.06

* cited by examiner

Primary Examiner—Robert Raevis
(74) Attorney, Agent, or Firm—Dennison, Schultz & Dougherty

(57) ABSTRACT

A calibration adaptor for a gas sensing device having a gas entry port therein includes a base piece having a gas entry port therein which is fixedly attached to a surface of the gas sensing device, and provided with means for releasably retaining the base piece in a first position in which the gas entry port of the gas sensing device is open to detect ambient gases, and means for moving the attached base piece to a second position in which the gas entry port of the base piece is aligned with the gas entry port of the gas sensing device, and controls entry of gas into the gas entry port of the gas sensing device. A calibration gas source may be attached to the gas entry port of the base piece.

17 Claims, 5 Drawing Sheets

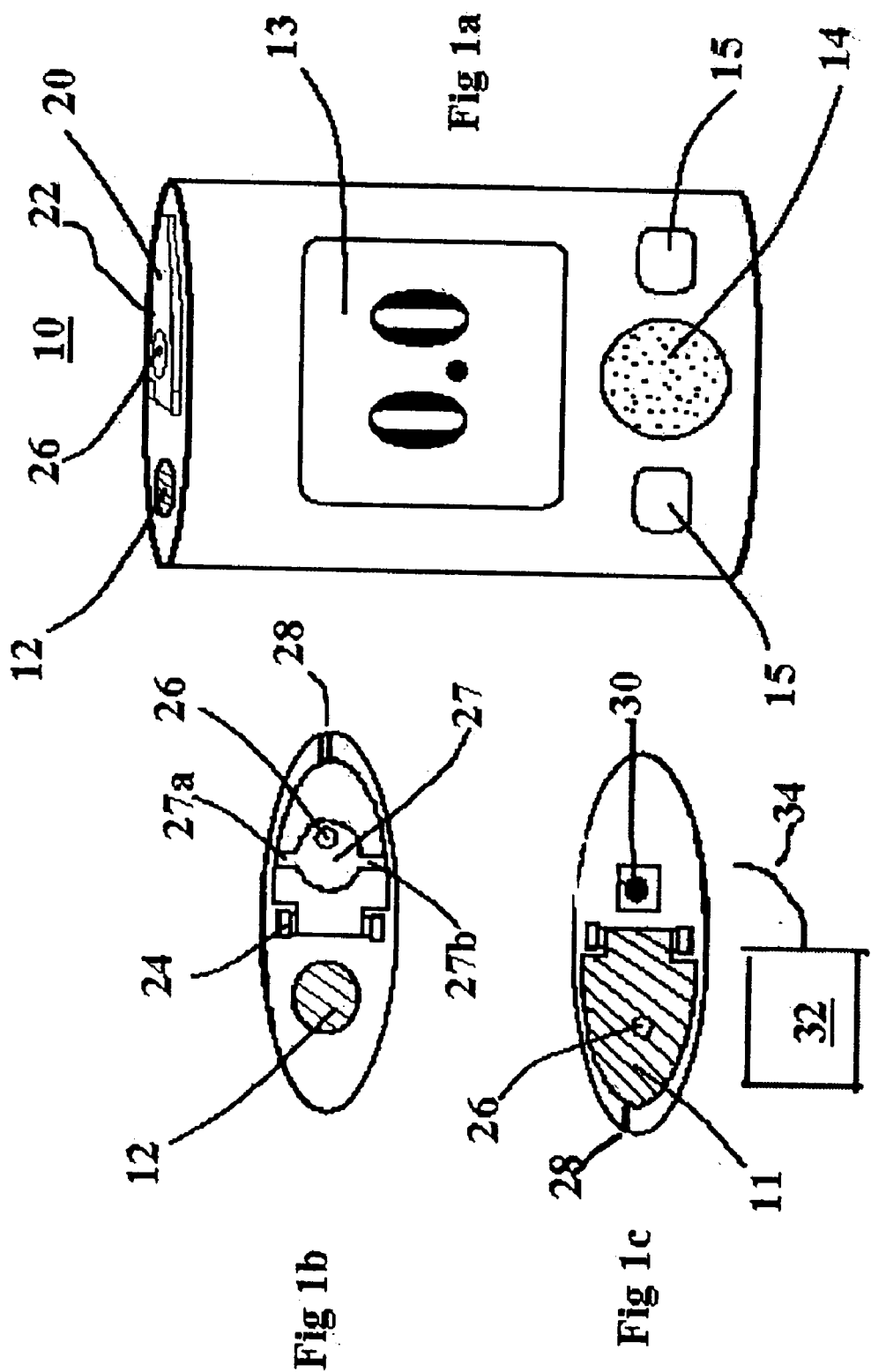

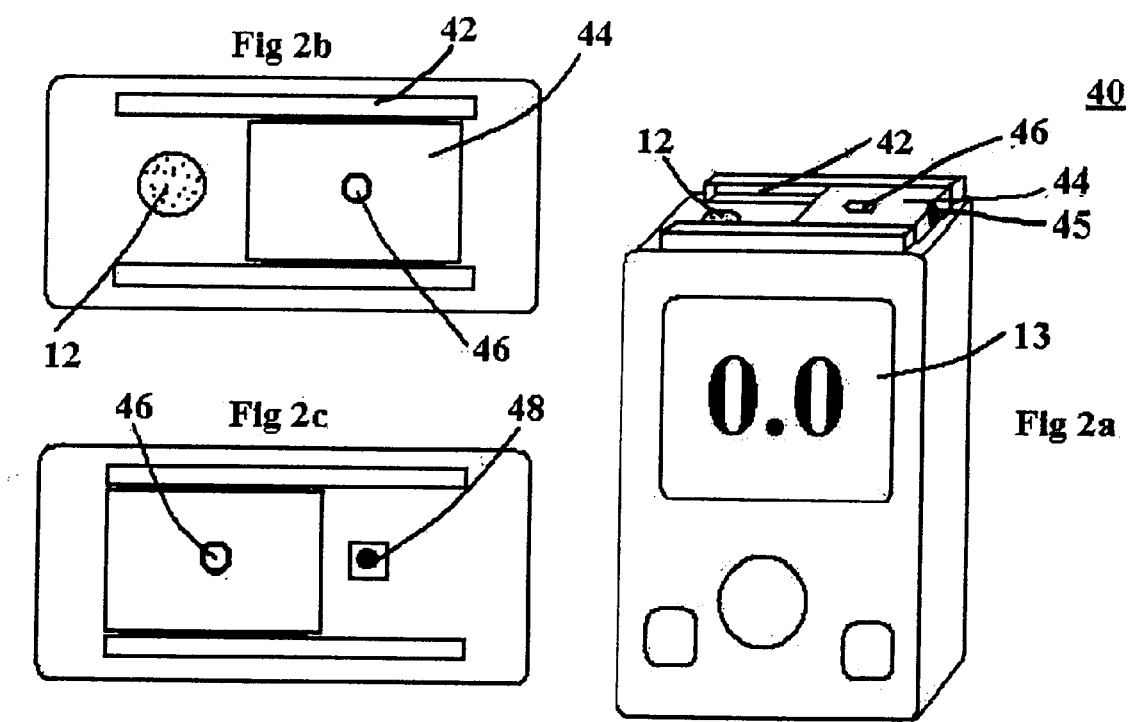

CALIBRATION ADAPTER FOR GAS DETECTION INSTRUMENT

BACKGROUND OF THE INVENTION

Instruments for gas detection are widely used to protect workers in potentially hazardous environments. Gaseous hazards may be due to the presence of flammable gases, toxic gases or oxygen concentrations higher or lower than normal air (20.9% v/v). Typical environments where hazardous atmospheres are encountered include oil production and petrochemical industries, steel and paper mills, sewers, water treatment plants, ship holds etc. Whenever workers need to be in a potentially hazardous atmosphere, they must have protection. Gas detection instruments provide this protection by continuously monitoring the atmosphere and if a potentially dangerous conditions exits, the gas detection instrument activates an alarm (typically visual, audible or vibration) to provide a warning of the hazard to the user.

Gas detection instruments typically contain one or more sensors that detect the potentially hazardous gases. There are many types of sensors, including electrochemical, optical, semiconductor, heat of combustion (e.g. catalytic bead) etc., but they all provide an electrical output that varies with the gas concentration. The technology of sensors is well known in the prior art; for example details of several commonly used sensors can be found in "Techniques and Mechanisms in Gas Sensing", Ed. P. T. Moseley, J. O. W. Norris, D. E. Williams, Publ. Adam Hilger, Bristol, 1991. ISBN 0-7503-0074-4.

Most sensors give a relative output, with, for example, the output current from an amperometric gas sensor being proportional to the gas concentration. While it may be possible to calculate the proportionality constant in principle (see for example P. R. Warburton et al., Analytical Chemistry (1998), 70, 998-1006), in practice the proportionality is almost always found by calibration. In the calibration process, a test gas of known concentration is applied to the gas detection instrument and the instrument reading is then adjusted to match the concentration of the test gas.

The calibration process is also repeated periodically with most gas detection instrumentation since the output of sensors can vary with time and conditions. The frequency of calibration depends on the stability of the sensor output with respect to time, the accuracy of the reading required and the gravity of the consequences if the reading is inaccurate. Since gas detection instruments for workplace safety are used to protect people's lives, these instruments are usually calibrated more frequently than instruments used in many other applications.

Gas detection instruments may be portable and in many cases they may be small enough to be worn. This type of use provides so called personal protection, since the instrument protects the individual worker. Another common mode of use is to mount the instrument to a wall or other object. These so called fixed instruments provide area monitoring.

In most cases, gas enters the instrument by diffusion. However, in some applications, the sample gas is pumped into the instrument by means of an internal or external pump.

The typical calibration frequency for an instrument using electrochemical or heat of combustion sensors is monthly. In calibration, it is important to ensure that the test gas is delivered to the sensor in a consistent manner from calibration to calibration. Furthermore, since the response of many types of sensors depends on the gas flow rate, it is important to ensure that the response of the sensor during calibration matches that during use. Thus for example, if a diffusion mode instrument is calibrated to 100 ppm carbon monoxide, then this instrument should read 100 ppm when placed in an atmosphere of 100 ppm carbon monoxide.

In order to ensure a repeatable and desired gas delivery to the instrument, calibration often involves use of a calibration adapter. A calibration adapter is a device that is usually attached to the instrument and covers or seals the gas path to the sensors. A regulated flow of gas, such as from a compressed gas cylinder is supplied to the calibration adapter. The calibration adapter performs two functions: it ensures that the gas delivery to the instrument during calibration is repeatable from calibration to calibration in any environment, and ensures that the sensor reading from the gas flow under calibration conditions matches the reading of the instrument when exposed to the same concentration of gas under normal use conditions.

Most manufacturers of gas detection instruments use calibration adapters. The calibration adapter is usually designed for a specific instrument or for a group of similar instruments and parts are usually not interchangeable with other instruments. Further details of gas detection instruments and calibration can be found in standard texts such as S. A. Ness "Air Monitoring For Toxic Exposures", Van Nostrand Reinhold, N.Y. (1991) and B. S. Cohen, S. V. Hering (Ed.), "Air Sampling Instruments for Evaluation of Atmospheric Contaminants", $8^{th}$ Edition, ACGIH, Cincinnati, Ohio (1995). Since calibration adapters are usually only used for calibration, they are often mislaid or lost and are no longer readily available for calibration. While new calibration adapters are available from the instrument manufacturers, time and resources can be wasted obtaining a calibration adapter and a needed calibration delayed.

SUMMARY OF THE INVENTION

It is therefore an object of the invention to provide a calibration adapter which is part of the gas detection instrument, ensuring that the calibration adaptor is always available for calibrating the instrument.

It is a further object of the invention to provide a calibration adapter which is mechanically attached to the instrument in such a way that it cannot be removed during normal use of the instrument.

To achieve these and other objects, the invention is directed to a calibration adaptor for a gas sensing device having a gas entry port therein, comprising:

a base piece having a gas entry port therein;

means for fixedly attaching the base piece to a surface of the gas sensing device, and allowing movement of the base piece between a first position in which the gas entry port of the gas sensing device is open to detect ambient gases, and a second position in which the gas entry port of the base piece is aligned with the gas entry port of the gas sensing device and controls entry of gas into the gas entry port of the gas sensing device;

means for releasably retaining the base piece in the first position;

means for releasably retaining the base piece in the second position; and means for attaching a calibration gas source to the gas entry port of the base piece.

In preferred embodiments of the invention, the calibration adapter can be in the form of a flap that is hinged or in the form of a slide. The calibration adaptor can then be in two positions, 1) normal operation and 2) calibration.

BRIEF DESCRIPTION OF THE DRAWINGS

FIG. 1a is a side plan view of an instrument according to the invention with a hinged calibration adapter, in the normal use position;

FIG. 1b is a top plan view of the instrument shown in FIG. 1a;

FIG. 1c is a top plan view of the instrument shown in FIG. 1a with a hinged calibration adapter in a calibration position;

FIG. 2a is a top plan view of an instrument according to the invention with a sliding calibration adapter in the calibration position;

FIG. 2b is a top plan view of the instrument shown in FIG. 2a;

FIG. 2c is a top plan view of the instrument shown in FIG. 2a with a sliding calibration adapter in calibration position;

DESCRIPTION OF THE PREFERRED EMBODIMENTS

Figures 3A, 3B:
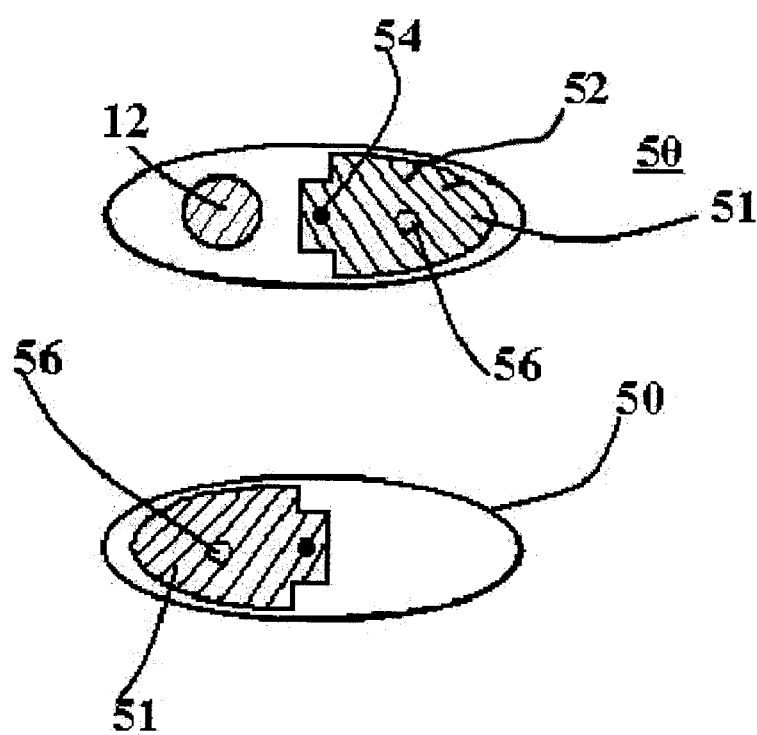
FIGS. 3a and 3b are top plan views of an alternate embodiment of an instrument according to the invention with a pivoting calibration adapter in the normal use position and calibration position, respectively.

In the calibration process for gas detection instruments, the calibration interval can vary from daily to annually depending on the type of sensor, the environment to which the instrument is exposed and the requirement for accuracy in the measurement. Typically, the initial step of the calibration process is to zero the instrument with clean air, clean air being defined as a gas mixture (usually ambient air) free of any components to which the sensor will respond, or which will cause an adverse effect on the sensor. The exception to this working definition is oxygen, since many instruments calibrate an oxygen sensor if present in clean air and zero the baselines of any other sensors present. Even though oxygen is an active gas on an oxygen sensor, its calibration is often performed during the zeroing process. In many cases the zeroing process is performed using clean air and then the user is required to ensure that the instrument is zeroed in an environment free from significant concentrations of active gases to which the sensor or sensors will respond.

The second part of the calibration process is application of the test gas containing components to which the sensor or sensors will respond. During this stage, the output from the instrument (display, alarm levels, etc.) is scaled so that the response of the instrument corresponds to the nominal value of the test gases when exposed to a gas of this concentration. For instruments with more than one sensor, or which are designed to detect more than one type of gas, several different gas mixtures may be applied to the instrument, or alternatively, test gas mixtures containing more than one active component may be used to calibrate the sensors.

The calibration process used to calibrate a gas detection instrument varies from manufacturer to manufacturer and even from instrument to instrument design. Therefore, many variations of calibration cycle and methodology are possible within the scope of this invention. This description is intended to illustrate the use of the integral calibration adapter rather than to specify a particular calibration protocol.

Many types of gas detectors are known in the prior art, both single gas detectors and multiple gas detectors that use a variety of sensor types (e.g. electrochemical, photoionization, catalytic bead, infrared, and optical among others). Gas detection instruments also vary in size from small personal gas monitors with dimensions less than 5 cm long and wide to much larger sizes. In addition, gas detection instruments can be portable or wall mounted (fixed). In general though, the instrument contains one or more sensors. The complexity of gas instruments varies from simple analog instruments without a display to complex microprocessor controlled devices with graphical displays and/or advanced communications (e.g. wireless or bus communications) to controllers or other systems. The sensors provide an electrical signal that is a function of the gas concentration. The invention described herein can be used with a wide diversity of gas detection instrument types and the description below is for illustrative purposes only. The internal design of gas detection instruments is well known in the prior art and will not be discussed herein.

FIGS. 1a–1c show a gas detection instrument 10 including a gas sensor (not shown) below gas port 12, a visual read-out display 13, an audible read-out speaker 14 and buttons 15 for changing the mode in which the gas detection instrument operates. A calibration adaptor 20 is disposed adjacent the gas port 12. During normal use (FIGS. 1a and b) the analyte gas enters the gas port 12 by natural convection and enters the sensor for analysis. The sensor provides an electrical signal that is a function of the gas concentration, and the instrument then amplifies this signal and converts it to, for example, a gas concentration reading on the display 13, or activates an audio, visual or vibrational alarm (e.g. from speaker 14), switches relay contacts etc. depending on the design of the instrument.

The calibration adapter 20 comprises a base piece 22 which is attached to the gas sensing instrument. In the embodiment of FIGS. 1a–1c, the means for this attachment is a hinge 24 fixed to the gas detection instrument, with the base piece movably fixed to the hinge, as is well known in the art. The base piece 22 includes its own gas entry port 26.

In normal use, the calibration adapter 20 is located away from the sensor gas diffusion path through the port 12, such that ambient gas has ready access to the sensor, as shown in FIGS. 1a and 1b. The base piece 22 includes a means 28 which locks the base piece to the sensor in this position. Such means may be a plastic snap but any other means of releasably locking the base piece in this position may be used.

The base piece 22 is movable, via hinge 24, between the first position, away from the gas entry port 12 of the gas sensing instrument and second position in which the gas entry port 26 is aligned with and covers the gas entry port 12, as shown in FIG. 1c. The base piece 22 is locked in place in this position by locking means 28.

When the user deems it necessary for a calibration to be performed on the instrument 10, the user lifts the calibration adapter base piece 22, rotates it about hinge 24 and locks the calibration adaptor 20 into the calibration position, shown in FIG. 1c. The instrument is then set into calibration mode, either manually, via buttons 15 or other controls such as a reed switch, or automatically. Advantageously, the gas detection instrument includes a switch 30 which automatically sets the instrument to calibration mode when the base piece is removed from the first position.

The prior art contains examples of automatic switches used to initiate calibration. For example, the model T80 instrument from Industrial Scientific Corporation, Oakdale, Pa., US has a magnet within the calibration adapter. When the calibration adapter is placed onto the instrument, the magnet activates a reed switch and thus sets the instrument into calibration mode. In contrast to the invention disclosed herein, the calibration adapter used for the T80 instrument is a separate device that is placed over the instrument in the conventional way to perform calibration.

Typically, the first step of a calibration is to zero the baseline of the one or more sensors in clean air by either supplying clean air to the instrument 10, or calibrating the instrument 10 in an environment containing clean air. If clean air is supplied to the instrument 10, then the same means is typically used as for the calibration gas described below. However, more commonly, the instrument 10 is zeroed in clean ambient air.

After zeroing the instrument 10, calibration gas containing a known concentration of an active gas is applied to the instrument 10 from a suitable source, e.g. a compressed gas cylinder 32 is connected to gas port 26 of the calibration adaptor 20 via tubing 34. The gas is applied for as long as necessary, as determined by the instrument manufacturer (3 minutes is typical) until the instrument 10 provides an indication that the calibration process is complete. This indication may be visual via the display 13 or by a beep or other conventional means. When the calibration process is complete, the base piece 22 position is changed from its calibration position over the sensor port 12 (FIG. 1c) back to its normal use position as shown in FIGS. 1a and 1b.

Often for diffusion-based instruments, it is not desirable to have the gas flow into the instrument 10, but instead have the gas flow over the sensor port 12, and the gas can then enter the sensor port 12 by diffusion. Therefore, the calibration adapter can also be designed with means for the gas to escape from the calibration adapter. For example, on one side of the base piece 22 there is a recess 27 surrounding the gas port 26, and this recess 27 surrounds the sensor port 12 of the instrument when the base piece is in the calibration position shown in FIG. 1c. This recess 27 is large enough to allow the gas to disperse over the area of the sensor port 12. Gas can escape from the calibration adapter 20 through gas passages 27a and 27b. These gas passages 27a and 27b ensure that the gas pressure underneath the calibration adapter 20 remains at atmospheric pressure; if the pressure exceeds atmospheric pressure, then the calibration will be more prone to error. The gas flow can be further moderated by incorporating porous sinters (not shown), or porous membranes (not shown) or both in the either the gas port 26 or the recess 27. The use of these components in calibration adapters is well known in the prior art and their function is to reduce the bulk flow of gas and thereby more closely approximate gas diffusion to the sensor below sensor port 12.

In another embodiment of this invention shown in FIGS. 2a–2c, the calibration adapter is not hinged, but rather slides along the top of the instrument. In this embodiment, the means for fixedly attaching calibration adaptor 40 is a pair of tracks 42 in which base piece 44 slides. Locking means 45 are provided at each end of the base piece 44 in order to lock the base piece 44 in either the first position, shown in FIGS. 2a and 2b, or the second position, shown in FIG. 2c. In the second position, a gas entry port 46 in the base piece 44 is aligned with the gas entry port 12 of the gas sensing device. A switch 48 is provided to change the gas sensing device to calibration mode. This embodiment operates in a manner identical to the embodiment shown in FIGS. 1a–1c.

In another embodiment shown in FIGS. 3a and 3b, a calibration adaptor 50 includes a base piece 52 which rotates about a pivot 54 which attaches the calibration adaptor to the gas sensing device. Rotation about the pivot moves the gas entry port 56 of the calibration adaptor into alignment with the gas entry port 12 of the gas sensing instrument, shown in FIG. 3b. Locking means for each of the two positions may also be provided.

Figure 4:
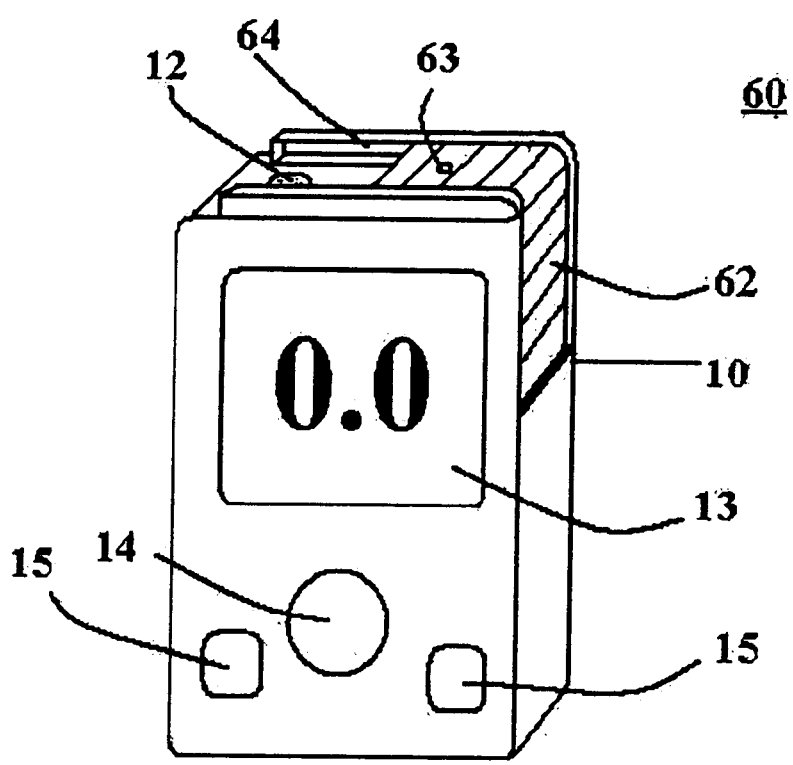
FIG. 4 is a plan view of an alternate embodiment of an instrument with a sliding calibration adapter in the calibration position.

In another embodiment shown in FIG. 4, calibration adapter 60 slides in a track around the side of the instrument 10 to the calibration position over sensor port 12. Such a sliding base piece 62 can be a single piece, or it can be comprised of several pieces mechanically linked together in similar fashion to form a rolling sectional door. In this embodiment, the base piece 62 with gas entry port 63 can be slid away from the sensor port 12 during normal use of the instrument. Typically, the base piece 62 will slide in a mechanical track 64, but other guide means can also be used.

The rolling door calibration adapter 60 of FIG. 4 is shown on the outside of the instrument for clarity of explanation. However, this calibration adapter can easily be built so that it resides within the instrument when not in use, for example, by extending the side wall of the instrument to create a recess for the rolling door, which is moved into position over the sensor port 12 when needed. An internal design has the advantages of better mechanical protection of the calibration adapter when not in use and a more ergonomic design of the instrument. The function and purpose of the calibration adapter is the same whether it is stowed internally or externally of the instrument. The calibration adapter can be positioned for normal use or for calibration by manual, mechanical or electrical means.

Many other embodiments of this invention can be envisioned. For example, the calibration adapter may be fixed in place over the instrument sensor port, but instead of a fixed single piece calibration adapter, the calibration adapter is made of many sections comprising a louver.

Typically the gas is supplied to the calibration adaptor for calibrating an instrument from compressed gas cylinders. Other gas sources are well known for calibrating gas monitors, for example permeation ovens and electrochemical gas generators. In most cases, the gas is delivered to the calibration adapter via a tube. Therefore it is advantageous if the gas entry port of the calibration adapter contains a receptacle to which one or more common sizes of flexible tubing can be attached. This receptacle is most conveniently a barbed fitting and is designed to be part of the gas entry port in a similar manner to current calibration adapters. Typical tubing sizes are 0.125, 0.375 and 0.25 inches (approximately 3 mm, 5 mm, 6 mm) outside diameter tubing, but other sizes are also be used.

Figure 5A:
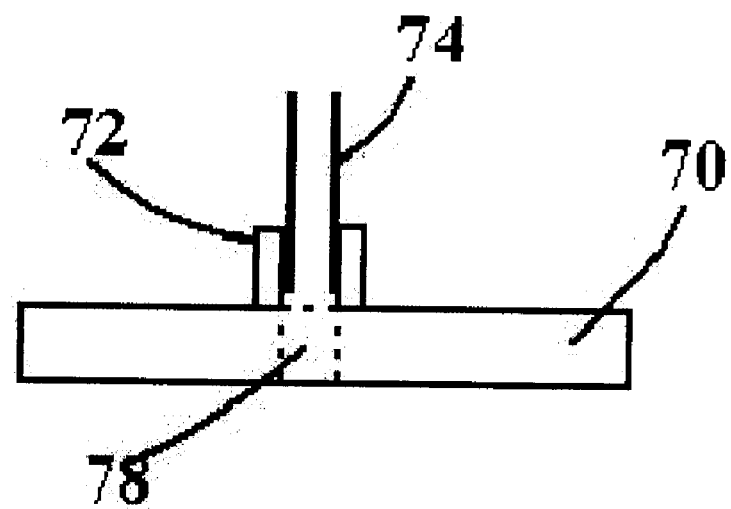
FIGS. 5a and 5b are side cross sectional views of a calibration adapter for use with an instrument according to the invention.
Figure 5B:
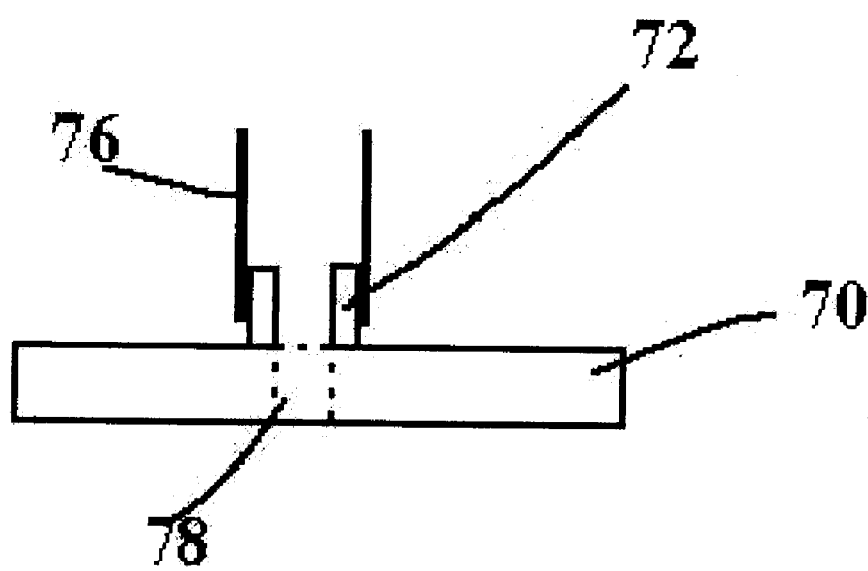

In another embodiment of the invention, the receptacle is designed so that the inner and outer diameters match two common tubing sizes, and the calibration adaptor can be used for both tubing sizes. An example of this design is shown in FIGS. 5a and 5b, in which a calibration adapter 70 corresponds the any of the calibration adapters discussed above. A raised tubing receptacle 72 is incorporated into the surface of the calibration adapter 70. A narrow bore tubing 74 can be attached to the calibration adapter by inserting the tubing 74 into the tubing receptacle 72 as shown in FIG. 5a. Alternatively, wide-bore tubing 76 can be attached to the calibration adapter 72 by placing the tubing 76 over the tubing receptacle 72 as shown in FIG. 5b.

The calibration adapter 70 should be designed so that the tubing 74 or 76 can attach to the tubing receptacle 72 and the gas can pass through gas port 78 in the calibration adaptor 70 in such a manner that is delivered to the sensor port.

In some applications it is advantageous to be able to draw in an air sample to the instrument for analysis. For example, such aspirated instruments are used to determine if the air within a manhole or other confined space is safe prior to entry by personnel. Typically a tube is inserted into the confined space and an air sample is withdrawn. If the air sample is found to be safe, then personnel can enter. If the air sample contains insufficient oxygen or contains hazardous components, then the personnel should not enter unless equipped with suitable safety equipment, such as a self-contained breathing apparatus (SCBA). The pump used to draw the air sample may be incorporated into the instrument or it may be an additional component of the instrument, or in some cases a manual pump is used. One of the advantages of the present invention is that it simplifies the conversion of the instrument from diffusion mode into aspirated mode. To use the instrument in diffusion mode, the calibration adaptor is placed in the normal use position (for example as shown in FIGS. 1a and 1b). To use the instrument in aspirated mode, the calibration adapter is placed in the calibration position, and the aspirated sample gas tube is connected to the calibration adapter in similar manner to the calibration gas delivery tube, as described above.

One further advantage of this invention is that the calibration adapter can be stowed away or put into place automatically. Thus, the movement of the calibration adaptor from the normal use position to the calibration position can be performed manually, or it can be performed mechanically under the control of a microprocessor or other electrical or mechanical controlling device. The means for implementation of this embodiment is well known to those persons experienced in the art of electrical and mechanical instrument design and other related technologies for example the design of electrical and mechanical camera lens covers.

While this invention has so far been described for use with portable gas detection equipment, it is equally applicable to fixed gas detection instruments, since it would be highly advantageous to avoid the need to transport a calibration adapter to every fixed gas detection head.

What is claimed is:

1. A calibration adaptor for a gas sensing device having a gas entry port therein, comprising:
   a base piece having a gas entry port therein;
   means for fixedly attaching the base piece to a surface of the gas sensing device, and allowing movement of the base piece between a first position in which the gas entry port of the gas sensing device is open to detect ambient gases, and a second position in which the gas entry port of the base piece is aligned with the gas entry port of the gas sensing device and controls entry of gas into the gas entry port of the gas sensing device;
   means for releasably retaining the base piece in the first position;
   means for releasably retaining the base piece in the second position; and
   means for attaching a calibration gas source to the gas entry port of the base piece.

2. A calibration adapter according to claim 1, wherein the means for attaching and allowing movement comprises a channel constructed and arranged for attachment to a first outer surface of the gas sensing device, the base piece being mounted for sliding in the channel between the first position and the second position.

3. A calibration adapter according to claim 2, wherein the channel is constructed and arranged to be mounted only on the first outer surface of the gas sensing device.

4. A calibration adapter according to claim 2, wherein the channel is constructed and arranged to be mounted on the first outer surface of the gas sensing device and on an adjacent second surface.

5. A calibration adapter according to claim 1, wherein the means for attaching and allowing movement comprises a hinge constructed and arranged for mounting on a first outer surface of the gas sensing device, the base piece being mounted for rotation about the hinge.

6. A calibration adapter according to claim 1, wherein the means for attaching and allowing movement comprises a pivot constructed and arranged for attachment to a first outer surface of the gas sensing device, the base piece being mounted for rotation about the pivot.

7. A calibration adapter according to claim 1, wherein the gas entry port includes a tubing receptacle having an outer diameter of size predetermined to accept a first size tubing to be attached thereto, and an inner diameter of size predetermined to accept a second size tubing to be attached thereto.

8. A calibration adapter according to claim 1, wherein the base piece comprises, adjacent the gas entry port of the calibration adapter, a recess therein constructed and arranged to permit gas to disperse over the gas entry port of the gas sensing device, and a gas passage from the recess extending outside of the base piece, to permit gas to escape from the recess.

9. A gas sensing device comprising:
   a gas entry port;
   means for analyzing gas which enters into the gas entry port;
   means for providing an indication of an analysis of gas which enters into the gas entry port; and
   a calibration adaptor fixedly attached to a surface of the gas sensing device, comprising:
      a base piece having a gas entry port therein;
      means for fixedly attaching the base piece to a surface of the gas sensing device, and allowing movement of the base piece between a first position in which the gas entry port of the gas sensing device is open to detect ambient gases, and a second position in which the gas entry port of the base piece is aligned with the gas entry port of the gas sensing device and controls entry of gas into the gas entry port of the gas sensing device;
      means for releasably retaining the base piece in the first position;
      means for releasably retaining the base piece in the second position; and
      means for attaching a calibration gas source to the gas entry port of the base piece.

10. A gas sensing device according to claim 9, additionally comprising a switch to change the device from a sensing mode to a calibration mode, said switch being constructed and arranged for activation by the base piece when the base piece is moved to the second position.

11. A device according to claim 9, wherein the means for attaching and allowing movement comprises a channel mounted to a first outer surface of the gas sensing device in which channel the base piece slides.

12. A device according to claim 11, wherein the channel is mounted only on said first outer surface of the gas sensing device.

13. A device according to claim 11, wherein the channel is mounted on the first outer surface of the gas sensing device and on an adjacent second surface.

14. A device according to claim 9, wherein the means for attaching a allowing movement comprises a hinge secured to an outer surface of the gas sensing device, about which hinge the base piece rotates.

15. A device according to claim 9, wherein the means for attaching a allowing movement comprises a pivot mounted on a first outer surface of the gas sensing device, about which pivot the base piece rotates.

16. A device according to claim 9, wherein the gas entry port comprises a tubing receptacle having an outer diameter of size predetermined to accept a first size tubing to be attached thereto, and an inner diameter of size predetermined to accept a second size tubing to be attached thereto.

17. A device according to claim 9, wherein the base piece comprises, adjacent the gas entry port of the calibration adapter, a recess therein constructed and arranged to permit gas to disperse over the gas entry port of the gas sensing device, and a gas passage from the recess extending outside of the base piece, to permit gas to escape from the recess.

* * * * *